United States Patent [19]
Giesselmann et al.

[11] Patent Number: 5,208,361
[45] Date of Patent: May 4, 1993

[54] METHOD OF PREPARING ALKYLISOTHIOCYANIC ACID ESTERS

[75] Inventors: Günter Giesselmann, Heusenstamm; Kurt Günther, Erlensee, both of Fed. Rep. of Germany

[73] Assignee: Degussa Aktiengesellschaft, Frankfurt, Fed. Rep. of Germany

[21] Appl. No.: 641,260

[22] Filed: Jan. 15, 1991

[30] Foreign Application Priority Data

Jan. 16, 1990 [DE] Fed. Rep. of Germany ....... 4001020

[51] Int. Cl.$^5$ ............................................. C07C 331/20
[52] U.S. Cl. ...................................................... 558/18
[58] Field of Search ............................................ 558/18

[56] References Cited

U.S. PATENT DOCUMENTS

| | | | |
|---|---|---|---|
| 3,637,788 | 1/1972 | Werth et al. | 558/18 |
| 3,787,472 | 1/1974 | Giesselmann | 558/18 |

FOREIGN PATENT DOCUMENTS 2105473  9/1972  Fed. Rep. of Germany ........ 558/18

OTHER PUBLICATIONS

German Article from Ullmanns Encyklopadie der technischen Chemie on "Thiocyanate und isothiocyanate Organische" pp. 154–159, (1975).

*Primary Examiner*—Mary C. Lee
*Assistant Examiner*—Michael G. Ambrose
*Attorney, Agent, or Firm*—Cushman, Darby & Cushman

[57] ABSTRACT

Alkylisothiocyanic acid esters having the formula R—N=C=S can be prepared by reacting N-alkyldithiocarbamates with hydrogen peroxide in aqueous phase at 95° to 130° C. The aqueous solution of N-alkyldithiocarbamate is reacted with a 20 to 40% by weight aqueous solution of hydrogen peroxide in a volumetric ratio of 1 to 0.8 to 1 while maintaining a pH of 1.5 to 4.5. The solutions are preferably sprayed into a reactor, at which time the alkylisothiocyanate formed distills off in vapor form and an aqueous phase containing the byproducts collects in the reactor. The method is capable of significantly increasing the space-time yield because much less sulfur is formed in comparison to the previously known method, which takes place at pH 5 to 9, thereby minimizing the shutdown times previously required for cleaning the reactor.

8 Claims, No Drawings

METHOD OF PREPARING ALKYLISOTHIOCYANIC ACID ESTERS

The present invention relates to a method of preparing alkylisothiocyanic acid esters by reacting N-alkyldithiocarbamates with aqueous hydrogen peroxide.

BACKGROUND OF THE INVENTION

Many methods are known for the preparation of alkylisothiocyanic acid esters, also designated as alkylisothiocyanates or alkyl mustard oils—cf. Ullmanns Enzyklopädie der technischen Chemie, 4th edition, volume 23, pp. 154–159 and Published German Patent Application DE-OS 21 05 473. With the exception of the method known from DE-PS 21 05 473, none of the previously known methods found acceptance in the art, either because the preparation of the raw materials was too expensive or because the yields of pure alkylisothiocyanates were too low.

The method of DE-OS 21 05 473 for the preparation of methylisothiocyanate, which is used as an intermediate product for organic syntheses as well as increasingly as a nematocide and a fungicide, did achieve industrial significance. The method of DE-OS 21 05 473 was applicable to the preparation of alkylisothiocyanic acid esters of the general formula R—N=C=S, in which R stands for a lower alkyl group. In that method, one mole of an aqueous solution of an N-alkyldithiocarbamate of the general formula R-NH-C(S)-SMe, in which R has the previously indicated significance and Me can stand for an alkali-metal atom, an ammonium group or alkylammonium group, is reacted at a temperature of 50° to 120° C. with at least 1 mole of a 20 to 70% by weight aqueous solution of hydrogen peroxide while maintaining a pH of 5 to 9. Then the alkylisothiocyanic acid ester which is formed is isolated in a known manner. According to the claims of DE-OS 21 05 473, it was preferred to use 2.3 to 2.5 moles hydrogen peroxide for each mole of dithiocarbamate and a pH of 6 to 8 was maintained; the use of a dithiocarbamate solution which was as concentrated as possible was considered to be especially advantageous. Half a mole sulfur and half a mole sulfate are produced as byproducts in this method at a molar ratio of dithiocarbamate to hydrogen peroxide of approximately 1 to 2.5 per mole alkylisothiocyanate. Whereas these byproducts can be separated readily on a laboratory scale when the method is carried out, the separation of the sulfur poses problems in large-scale industrial production; the sulfur accumulates in part as hard lumps, and, in addition, the reactor can become encrusted. Frequent and often lengthy interruptions of the operation are necessary for removing the lumps and encrustations. This considerably reduces the space-time yield of the method.

SUMMARY OF THE INVENTION

The object of the present invention is to improve the method of preparing alkylisothiocyanic acid esters of the formula R—N=C=S, in which R signifies a methyl or ethyl group, from an aqueous solution of an N-alkyldithiocarbamate of the formula R—NH—C(S)—S—Me, in which R stands for a methyl or ethyl group and Me for an alkali-metal atom or an ammonium or alkylammonium group, and from an aqueous solution of hydrogen peroxide, using at least one mole hydrogen peroxide for each mole N-alkyldithiocarbamate. The reaction is carried out at a temperature of 95° to 130° C. and the alkylisothiocyanic acid ester formed is separated in a known manner from the reaction mixture. A further object of the present invention is to carry out that reaction in such a manner that a high yield is achieved, the product is obtained in high purity, the space-time yield is increased and the expenditure for the cleaning of the reactor is reduced.

These and other objects are achieved by reacting the aqueous solution of N-alkyldithiocarbamate with a 20 to 40% by weight aqueous solution of hydrogen peroxide in a volumetric ratio of 1:08–1 while maintainng a pH of 1.5 to 4.5.

Surprisingly, sodium thiosulfate is produced, but hardly any elementary sulfur is accumulated. As is apparent from the examples, the amount of sulfur which is formed is only 5 to 10% of the amount which would have been expected under the reaction conditions of the previously known method. As a result of the reduced production of sulfur, removal of the sulfur suspended in the aqueous phase of the reactor poses no problems. The method of the invention thus permits uninterrupted operation both in the discontinuous and in the continuous mode so that, at a given reactor size, the conversion in moles/hour could be almost doubled without a reduction of the yield. According to the invention, methyl and ethylisothiocyanate are obtained in a purity of approximately 98% and in a yield of approximately 80 to 95%.

The reaction of the aqueous N-alkyldithiocarbamate solution with the aqueous solution of hydrogen peroxide takes place at 95° to 130° C., preferably 100° to 120° C. At least 1 to 3 moles, preferably 2 to 2.5 moles hydrogen peroxide are used per mole N-alkyldithiocarbamate. The $H_2O_2$ concentration is in a range of 20 to 40% by weight. Aqueous $H_2O_2$ solutions with 25 to 35% by weight $H_2O_2$ such as those readily available by diluting more highly concentrated solutions, e.g. those with 50 to 70% by weight, are preferably used. The dilution can optionally also take place during the addition of the solution of hydrogen peroxide into the reaction area, e.g. by simultaneously spraying a rather concentrated hydrogen peroxide solution and water so that the desired concentration is achieved.

The concentration of the aqueous N-alkyldithiocarbamate solution should preferably be in a range of 30 to 45% by weight. The pH of the solution is adjusted to 9.5 to 12.0. The preparation of such solutions takes place in a known manner; the solution of the sodium-N-alkyldithiocarbamate can be obtained from the alkylamine, carbon disulfide and sodium hydroxide solution.

The reaction of the two solutions takes place in the claimed volumetric ratio in such a manner that a pH of 1.5 to 4.5, preferably 2.0 to 4.0 is maintained in the aqueous phase. By contrast, no volumetric ratio of the N-alkyldithiocarbamate solution to the solution of hydrogen peroxide was disclosed for the previously known method of DE-PS 21 05 473, according to which the pH should be between 5 and 9; however, such a ratio results from the examples in a range from 1:0.45–0.75, which is thus outside of the method of the present invention.

The reactant solutions can be brought together from separate feed lines to the reactor. At the reaction temperature of 95° to 130° C., the alkylisothiocyanate is generally separated immediately after its formation in vapor form from the aqueous phase containing the byproducts. The carbon disulfide which develops due to the slight decomposition of dithiocarbamate is quantitatively recovered by distillation of the raw alkylisothiocyanate and can be supplied to the preparation of the dithiocarbamate.

The isolation of the alkylisothiocyanic acid esters takes place in a known manner, e.g. by extraction by means of e.g. ketones, aliphatic or aromatic hydrocarbons, methylene chloride, chloroform, carbon tetrachloride, carbon disulfide, ethers, esters or nitrobenzene. However, separation by means of azeotropic distillation, which can also take place with the addition of water vapor, is more advantageous, especially if the method is carried out in a continuous manner. The yield can be significantly raised by this means. The very high exothermic nature of the reaction of the dithiocarbamate with the hydrogen peroxide can also be utilized to supply heat for the distillation. The heat available from the reaction is so great that no additional energy is required for the distillation of the isothiocyanic acid ester.

According to an especially preferred embodiment, the aqueous N-alkyldithiocarbamate solution and the aqueous solution of hydrogen peroxide are reacted with one another in the form of droplets, especially very finely distributed droplets. Conventional devices for converting a liquid into droplet form are suitable. A fine distribution of the components is preferably achieved by using nozzles which can include either single-substance or multi-substance nozzles. One or more nozzles can be located in the reactor, e.g. in the cover and/or in the upper part of the wall.

The spray angle of the nozzles is designed in such a manner in accordance with the reactor size that the main reaction takes place in the center of the upper third of the reactor in order to avoid condensation on the inner wall. The reactor is filled before the start of the reaction in accordance with its volume to approximately ⅛ to approximately ⅓ with water. In the case of a continuous mode of operation, the byproducts which form are constantly removed from the reactor and, to the extent necessary, replaced by water.

DETAILED DESCRIPTION OF PREFERRED EMBODIMENTS

The following examples illustrate preferred embodiments of the invention.

EXAMPLE 1

A heatable and coolable reactor is provided which has a spray device for the solutions to be reacted with each other, an agitator, a vapor outlet, a bottom outlet and devices for measuring pH and temperature. The reactor is filled to 15% of its volume with water. After the aqueous materials in the reactor has been heated to approximately 98° C., 3 moles (770 ml) of an aqueous 42% by weight N-methyldithiocarbamate solution, prepared in a known manner from methylamine, carbon disulfide and sodium hydroxide and adjusted to pH 10, is reacted with 7.5 moles (700 ml) of a 32.5% by weight aqueous solution of hydrogen peroxide volumetric ratio of the solutions 1:0.91, molar ratio of the reactants, 1:2.5. To this end, the aqueous N-methyldithiocarbamate solution and the aqueous solution of hydrogen peroxide are brought together using a nozzle with an inner diameter of 2 mm and sprayed in a very finely distributed manner into the reactor. The methylisothiocyanate formed is distilled off immediately after it has been produced. The pH of the liquid phase in the reactor bottom and the temperature at the vapor outlet are monitored during the reaction—cf. Table 1.

TABLE 1

| Time (min.) | pH | Temperature (°C.) |
| --- | --- | --- |
| 15 | 2.1 | 100.6 |
| 30 | 2.4 | 100.1 |
| 45 | 2.6 | 100.7 |
| 60 | 2.5 | 101.6 |
| 75 | 2.5 | 102.9 |
| 90 | 2.0 | 102.8 |

The heat generated by the reaction is so great that no additional energy is required for the distillation of the methylisothiocyanate. In order that the methylisothiocyanate separates as a liquid, the temperature of the condenser is adjusted to 35° to 38° C. Approximately 5 to 7% methylisothiocyanate is still dissolved in the water which distills simultaneously with the methylisothiocyanate, which methylisothiocyanate can be separated by means of extraction with n-hexane. (This separation can also take place in an alternative manner by distillation of the aqueous phase.)

2.6 moles 98% methylisothiocyanate are obtained, corresponding to a yield of 87%; 4 g sulfur, that is, only 8.3% of the amount to be expected in the previously known method, are suspended in the aqueous phase (reactor bottom).

EXAMPLE 2

770 ml (3 moles) 42% by weight aqueous N-methyldithiocarbamate solution adjusted to pH 11.0 are reacted with 650 ml (7.5 moles) of a 35% by weight aqueous solution of hydrogen peroxide in a manner analogous with Example 1—volumetric ratio of the solutions 1:0.84, molar ratio of the reactants 1:2.5. The pH of the liquid phase and the temperature at the vapor outlet during the reaction are shown in Table 2.

TABLE 2

| Time (min ) | pH | Temperature (°C.) |
| --- | --- | --- |
| 15 | 3.9 | 99 |
| 30 | 4.2 | 99 |
| 45 | 3.6 | 100 |
| 60 | 3.6 | 100 |
| 75 | 3.6 | 101 |
| 90 | 3.7 | 101 |

2.51 moles 98% methylisothiocyanate are obtained, corresponding to a yield of 84%; the aqueous phase contains 5 g sulfur (10.4% of the theoretically possible amount).

EXAMPLE 3

770 ml (3 moles) 42% by weight N-methyldithiocarbamate solution adjusted to pH 10 are reacted with 644 ml (6.9 moles) of a 32.5% by weight aqueous solution of hydrogen peroxide analogous to Example 1—volumetric ratio of the solutions 1:0.84, molar ratio of the reactants 1:2.3. The pH of the liquid phase and the temperature at the vapor outlet during the reaction are shown in Table 3.

TABLE 3

| Time (min.) | pH | Temperature (°C.) |
| --- | --- | --- |
| 15 | 4.5 | 99 |
| 30 | 4.2 | 100 |
| 45 | 4.4 | 101 |
| 60 | 4.3 | 101.5 |
| 75 | 4.3 | 102 |

TABLE 3-continued

| Time (min.) | pH | Temperature (°C.) |
| --- | --- | --- |
| 90 | 4.3 | 103 |

2.45 moles 98% methylisothiocyanate are obtained, corresponding to a yield of 82%; the aqueous phase contains 3.7 g sulfur (7.7% of the theoretically possible amount).

EXAMPLE 4

770 ml (3 moles) 42% by weight aqueous N-methyldithiocarbamate solution adjusted to pH 10 are reacted with 760 ml (7.5 moles) of a 30% by weight aqueous solution of hydrogen peroxide analogous to Example 1—volumetric ratio of the solutions 1:0.99, molar ratio of the reactants 1:2.5. The pH and the temperature during the reaction are shown in Table 4.

TABLE 4

| Time (min.) | pH | Temperature (°C.) |
| --- | --- | --- |
| 15 | 4.0 | 100 |
| 30 | 3.5 | 101 |
| 45 | 3.2 | 101.5 |
| 60 | 3.2 | 101.5 |
| 75 | 2.5 | 102 |
| 90 | 2.8 | 102.5 |

Approximately 2.45 moles 98% methylisothiocyanate are obtained, corresponding to a yield of 82%; the aqueous phase contains 3 g sulfur (6.2% of the theoretically possible amount).

EXAMPLE 5

770 ml (3 moles) 42% by weight aqueous N-methyldithiocarbamate solution adjusted to pH 10 are reacted with 700 ml (7.5 moles) of a 32.5% by weight aqueous solution of hydrogen peroxide in a manner analogous with Example 1—volumetric ratio of the solutions 1:0.91, molar ratio of the reactants 1:2.5. During the reaction, 350 g water vapor are additionally blown into the reaction area. The pH and the temperature during the 90-minute reaction are shown in Table 5.

TABLE 5

| Time (min.) | pH | Temperature (°C.) |
| --- | --- | --- |
| 15 | 2.2 | 100.5 |
| 30 | 2.3 | 100.6 |
| 45 | 2.0 | 101.2 |
| 60 | 1.9 | 101.8 |
| 75 | 2.1 | 102.3 |
| 90 | 2.0 | 102.5 |

2.7 moles 98% methylisothiocyanate are obtained, corresponding to a yield of 90%; 3.5 g sulfur (7% of the theoretically possible amount) are suspended in the aqueous phase.

EXAMPLE 6

515 ml (1.5 moles) 36% by weight aqueous N-ethyldithiocarbamate solution adjusted to pH 10 and prepared in a known manner from ethylamine, carbon disulfide and sodium hydroxide solution are sprayed within 90 minutes with 410 ml (3.75 moles) 31% by weight aqueous solution of hydrogen peroxide in a manner analogous with Example 1. The volumetric ratio of N-ethyldithiocarbamate solution to the solution of hydrogen peroxide corresponds to 1:0.8, the molar ratio of the reactants to 1:2.5. The pH of the liquid phase (reactor bottom) and the temperature at the vapor outlet during the reaction are shown in Table 6.

TABLE 6

| Time (min.) | pH | Temperature (°C.) Vapor Outlet |
| --- | --- | --- |
| 15 | 3.2 | 100.2 |
| 30 | 3.0 | 100.7 |
| 45 | 2.9 | 101 |
| 60 | 3.0 | 101.6 |
| 75 | 2.8 | 102 |
| 90 | 2.9 | 102.3 |

1.38 moles 98% ethylisothiocyanate, corresponding to a yield of 92.4%, and 2 g sulfur (8.3% of the theoretically possible amount) are formed.

What is claimed is:

1. In a method of preparing alkylisothiocyanic acid esters of the formula R—N=C=S, in which R signifies a methyl or ethyl group, from an aqueous solution of an N-alkyldithiocarbamate of the formula R—NH—C(-S)—S—Me, in which R stands for a methyl or ethyl group and Me for an alkali-metal atom or an ammonium or alkylammonium group, and from an aqueous solution of hydrogen peroxide, using at least one mole hydrogen peroxide for each mole of N-alkyldithiocarbamate, the reaction being carried out at a temperature of 95° to 130° C. and the alkylisothiocyanic acid ester formed being separated in known manner from the mixture;

the improvement in which the aqueous solution of N-alkyldithiocarbamate is used in the form of a 30 to 45% by weight aqueous solution having a pH of 9.5 to 12 and it is reacted with a 20 to 40% by weight aqueous solution of hydrogen peroxide in a volumetric ratio of 1 to 0.8 to 1 while maintaining a pH of 1.5 to 4.5, the aqueous solution of N-alkyldithiocarbamate and the aqueous solution of hydrogen peroxide being reacted with one another in the form of droplets.

2. A method as set forth in claim 1 in which a 25 to 35% by weight aqueous solution of hydrogen peroxide is used.

3. A method as set forth in claim 1 in which the reaction is carried out at a temperature of 100° to 120° C.

4. A method as set forth in claim 1 in which 2 to 2.5 moles hydrogen peroxide are used for each mole of N-alkyldithiocarbamate.

5. A method as set forth in claim 1 in which the pH in the reaction mixture is maintained in the range of 2.0 to 4.0.

6. A method as set forth in claim 1 in which the alkylisothiocyanic acid ester is removed in vapor form from the reaction area.

7. A method as set forth in claim 1 in which the method is carried out in a continuous manner by separating the alkylisothiocyanic acid ester and byproducts which are volatile under the reaction conditions immediately after their formation in a vapor form and by separating the nonvolatile byproducts with the aqueous phase from the reaction area and, to the extent required, by maintaining the liquid level in the reactor by means of the addition of water.

8. A method as set forth in claim 1 in which additional water vapor is blown into the reactor during the reaction.

* * * * *